(12) United States Patent
Hofeldt et al.

(10) Patent No.: US 7,957,000 B2
(45) Date of Patent: Jun. 7, 2011

(54) WEB INSPECTION CALIBRATION SYSTEM AND RELATED METHODS

(75) Inventors: David L. Hofeldt, Oakdale, MN (US); Derek H. Justice, Cottage Grove, MN (US); John A. Ramthun, Hudson, WI (US); Catherine P. Tarnowski, Mahtomedi, MN (US); Wenyuan Xu, Oakdale, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 6 days.

(21) Appl. No.: 12/786,975

(22) Filed: May 25, 2010

(65) Prior Publication Data

US 2010/0231897 A1    Sep. 16, 2010

Related U.S. Application Data

(62) Division of application No. 12/133,487, filed on Jun. 5, 2008, now Pat. No. 7,773,226.

(51) Int. Cl.
*G01N 21/84* (2006.01)
(52) U.S. Cl. .................................................. 356/429
(58) Field of Classification Search .................. None
See application file for complete search history.

(56) References Cited

U.S. PATENT DOCUMENTS

| | | | |
|---|---|---|---|
| 3,562,525 A | 2/1971 | Constantine et al. | |
| 3,671,744 A | 6/1972 | Constantine | |
| 4,566,798 A | 1/1986 | Haas | |
| 5,071,514 A | 12/1991 | Francis | |
| 5,563,809 A | 10/1996 | Williams et al. | |
| 5,666,199 A | 9/1997 | Hess et al. | |
| 6,264,533 B1 | 7/2001 | Kummeth et al. | |
| 6,452,679 B1 | 9/2002 | Workman, Jr. | |
| 6,553,133 B1 | 4/2003 | Sari-Sarraf et al. | |
| 6,721,045 B1 * | 4/2004 | Hunter | 356/237.5 |
| 6,813,032 B1 * | 11/2004 | Hunter | 356/601 |
| 6,829,516 B2 | 12/2004 | Popp et al. | |
| 6,850,857 B2 | 2/2005 | Ignagni et al. | |
| 6,934,028 B2 | 8/2005 | Ho et al. | |
| 6,967,721 B2 | 11/2005 | Moshe | |
| 7,002,676 B2 | 2/2006 | Akiyama | |
| 7,773,226 B2 | 8/2010 | Hofeldt et al. | |
| 2007/0125936 A1 | 6/2007 | Nash et al. | |

FOREIGN PATENT DOCUMENTS

JP    06-018416    1/1994
JP    2004-226128    8/2004

OTHER PUBLICATIONS

International Search Report, PCT/US2009/041596, 3 pages.

* cited by examiner

*Primary Examiner* — Tu T Nguyen
(74) *Attorney, Agent, or Firm* — Steven A. Bern (57) ABSTRACT

Systems and methods for calibrating a web inspection system.

10 Claims, 4 Drawing Sheets

WEB INSPECTION CALIBRATION SYSTEM AND RELATED METHODS

CROSS REFERENCE TO RELATED APPLICATIONS

This application is a divisional of U.S. Ser. No. 12/133,487, filed Jun. 5, 2008 now U.S. Pat. No. 7,773,226, now allowed, the disclosure of which is incorporated by reference in its entirety herein.

BACKGROUND

Certain web properties lend themselves to optical inspection. Such properties may either be directly observable (such as transmissivity, or aberrations such as scratches or other cosmetic defects) or be sufficiently correlated to an optically-observable property as to be measurable. For example, for a non-woven web, a property correlated with an optically-observable property, but not directly observable, is its insulating capability, which is often measured by thermal conductivity. A web's thermal conductivity can be measured by monitoring the rate of heat flux across a known temperature gradient, but such measurement is difficult in on-line, production-type environments. However, if the web's construction allows for light transmission, its thermal conductivity may be correlated to the brightness of light transmitted through it and into a series of optical sensors. Thus, using the optical signal of light transmitted through the web, the web's thermal conductivity can be characterized using known optical sensing technologies, provided the optical signal can be calibrated to thermal conductivity units. Thermal conductivity is just one example of a property that may be measured by optical inspection techniques. Other example properties include surface roughness, thermal diffusivity, porosity, crystallinity, and thickness, to name a few, as well as of course optical properties like optical density, transmissivity, reflectivity, and birefringence.

An issue for quantitative inspection schemes (and to a lesser degree qualitative inspection schemes) is the calibration of the sensor or sensors that comprise the web inspection system such that it yields data about the web property of interest in units of measurement calibrated to be within some margin of error of a known standard.

SUMMARY

Systems and methods for calibrating a web inspection system are disclosed. More specifically, systems and methods for real-time, on-line calibration of a web inspection system are disclosed. Generally, these systems and methods involve the use of a sensor up-web (or down-web) from the web inspection system, the sensor configured to accurately measure a web property of interest in calibrated units. Information provided from this sensor is used to enable calibration constants for the web inspection system to be computed real-time or near real-time, most often without interrupting the normal manufacturing process of the web. In various embodiments, this calibration system may eliminate the need for down-time or resource-intensive tests associated with traditional approaches to web inspection system calibration. Further, using the systems and methods disclosed herein, a web inspection system may be configured to provide quantitative information about a web property in engineering units. In some embodiments, quantitative information may be used to compare properties of web processes on different lines, or compare data across web inspection systems, or analyze the performance of the same web inspection system over single or multiple runs.

DETAILED DESCRIPTION

Web inspection systems consist of quantitative and qualitative embodiments. A quantitative inspection system yields inspection information about a web property in units calibrated to a known standard, for example in engineering units. This is contrasted with qualitative inspection systems, which focus on the relative change of a web property over time. Qualitative inspection systems may be sufficient to recognize signal patterns indicative of particular process defects (such as chatter, die lines, mottle, and other typical non-uniformities). However, as qualitative inspection systems rely on no absolute target levels or calibration procedures, they yield no reproducible metric (or set of metrics) that can be used by an operator to track whether the web process is in control, or whether changes to the process have reduced the web's level of non-uniformity from one run to the next.

Sensors and imaging systems used for inspecting web-based products must be calibrated periodically. The particular calibration schedule depends on such things as the type of web being inspected, and that web's property of interest that is subject to the inspection. Additionally, environmental conditions in the operating environment (temperature, humidity, dust levels, and so forth) and production and maintenance schedules may cause inspection systems to go out of calibration, and thus necessitate calibration every few days, every few hours, or possibly even more frequently. Approaches to calibrating optical sensing equipment for web inspection generally fall into one or more of several categories.

First, the "off-line" approach to calibrating a web inspection system involves recording the signal (optical or otherwise) produced by the web inspection system when that system is exposed to a known sample or known set of samples. In the case of an optical inspection system, this is often done by placing a series of samples into the optical path or paths of the inspection system, possibly at multiple positions. This off-line approach requires that normal web processing or production be interrupted while samples are placed into the location normally occupied by the web. A variation on this off-line approach is to move the web inspection system (including illumination devices) to an off-web position, generally adjacent to the line and outside the web path, where the sensing response associated with a standard sample or samples can be recorded, and thus the web inspection system calibrated. After calibration the web inspection system is restored to its web-inspection position. While the inspection system if off-line, being calibrated, web processing may proceed, but absent a second inspection system (which is costly), such processing may not be within control.

A second approach attempts to obtain calibration data while normal web is being produced, that is, using as-produced web, albeit with as yet unknown properties. To do this, the inspection system records data from a first section of web whose location is either marked or otherwise known to the web handling system. When the first section of web reaches the winder, it is cut from the remainder of the web, usually as an "end-of-roll" sample, and taken to a quality control lab. Provided that accurate location information is available such to allow positions on the sample to be registered with the data stored by the inspection system when the sample passed through the inspection station, off-line quality control instruments can be used to provide calibration data for the inspection system. This approach is resource intensive and requires careful attention to sample registration to achieve good data, and also suffers from a substantial time lag between when the sample initially passed through the inspection station and when the calibration becomes available.

A third approach involves some combination of the above two approaches. For example, a known sample may be placed outside the edges of the normal web path, but within the area viewed by the inspection system. This provides ongoing calibration data for the outermost sensor elements while product is still running. However, transferring calibrations to web inspection system sensor(s) over the normal web, whose properties are unknown, requires knowledge of the relation between the responses of the inner sensor elements and the responses of the outer sensor elements, and those responses must remain fixed relative to each other at all times. In another example, calibration samples are exposed to various portions of the inspection system's field-of-view, thus adding additional known offsets to the unknown properties of the web. This places some restrictions on the statistical variations of the web during calibration, and also changes the range that the inspection system may have to operate over.

The multiple point calibrations of an inspection system required for the approaches described above are tedious and may require a relatively large number of human operators, a large capital investment in an automated calibration system, or a combination of both. Further, changes to components that comprise the inspection system (for example the intensity distribution of a light source providing illumination to a camera, or the alignment between the source and receiving optics in a laser scanner) necessitate further calibration(s).

Figure 1:
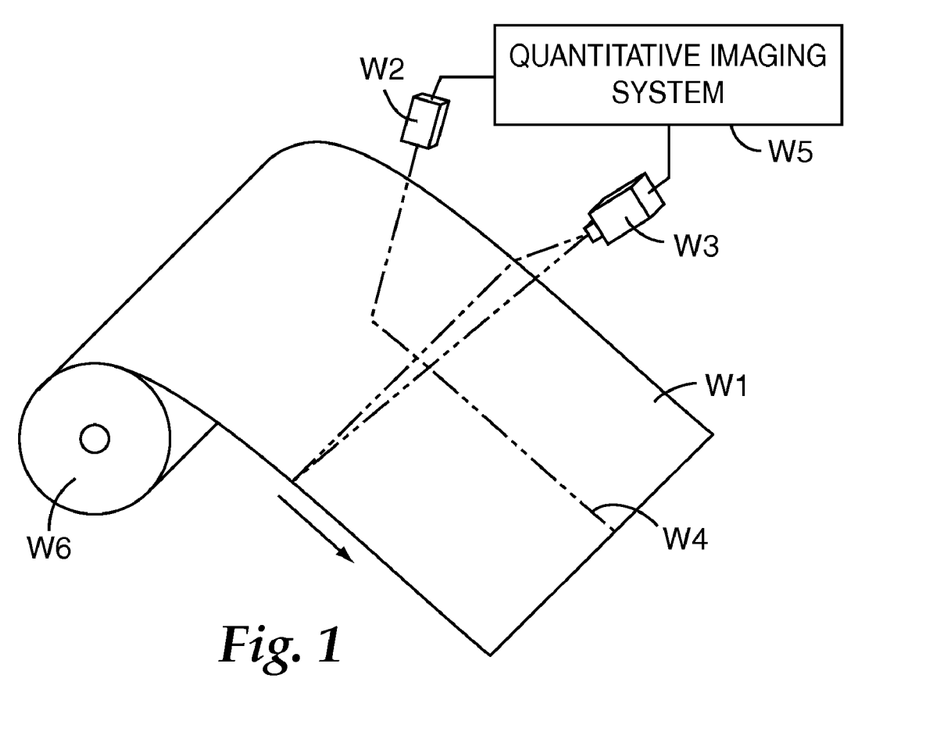
FIG. 1 is a schematic of a calibration system.

FIG. 1 shows a schematic of one embodiment of a calibration system on web handling system W6. Web handling system W6 may be any web handling system used for manufacturing, converting, processing, or inspecting web W1. Web W1 may be any material substantially wider than it is thick that is amenable to automated inspection. For example, web W1 may be an optical film, a battery membrane material, a paper, a type of woven material, a type of non-woven material, an abrasive, a micro-structured film, a multi-layered film, a composite film, a printed and patterned web, a foil, or sheet goods (like rolled steel). Web W1 may have one or more coatings, such as wet coatings. Additionally, web W1 may be a web of pieces molded to form a web, or molded onto a web.

Web W1 moves from left to right, possibly as part of a manufacturing or converting process. Sensor W2 is shown positioned up-web from web inspection system W3 but it could also be positioned down-web from web inspection system W3. In one embodiment, sensor W2 could even be positioned so as to receive signals from the same web area as web inspection system W3. In such embodiment, one or more beamsplitters could be used on signals emanating from a web area (provided both the sensor W2 and web inspection system W3 are based on optical signals).

Sensor W2, in one embodiment, is a single readout sensor configured to receive inspection signals emanating from a single lane W4 of web W1, and then generate signals indicative of this response. Sensor W2 may be any type of sensor—for example it may be an optical sensor (sensitive to, for example, visible light, ultraviolet, infra-red, or near infra-red, or employing terahertz imaging techniques), or a sensor configured to receive some type of electromagnetic radiation, or a sensor configured to receive acoustic waves. Sensor W2 is calibrated to accurately measure a property of web W1 in calibrated units. It is not necessary that sensor W2 be a single point sensor, but the calibration transfer to the web inspection system described below uses a single data stream. Where sensor W2 is not a single point sensor, a single data stream may be provided by averaging signals from several adjacent sensing elements that comprise sensor W2 (camera pixels, capacitive sensing elements, and so forth) to obtain a single data stream. There is no strict limit to the number of sensing elements that comprise sensor W2, however, the more elements there are in sensor W2, the more difficult it may become to assure they are all calibrated to the same response relative to one another.

Web inspection system W3 is, in one embodiment, a line-scan camera, which at least receives inspection signals associated with the same single lane W4 as single output sensor W2, as well as a lane other than lane W4. A line-scan camera is relatively inexpensive and ubiquitous, but the same or similar calibration techniques and systems as described herein could accommodate other types of inspection systems. For example, rather than line-scan cameras, web inspection system W3 may also comprise laser scanners, time-delay integration cameras, area scan cameras, other array sensors, or some combination of these systems. Web inspection system W3 may receive signals from a width of web W1 that is less than the entire width.

Sensor W2 is periodically calibrated against a known standard. The timing of sensor W2 calibration is dependant on the propensity of the sensor to drift out of calibration and the tolerances required for a particular web processing environment. For example, an optical density gauge used as sensor W2 can be configured to measure the light transmission of a web within a particular wavelength band, but as the light source ages, its spectral output and/or power levels might change so as to affect the accuracy of the data coming from the sensor. The response of such a sensor could be checked periodically using a known standard or set of standards to correct for such a drift.

The calibration of a sensor W2, as compared with the calibration of a web inspection system such as a line scan camera, is a rather trivial matter and may be accomplished in one embodiment by swinging the single output sensor off-line to receive signals from a known standard or set of standards. Alternatively, the sensor W2 may be calibrated using known techniques in a quality control laboratory located near the manufacturing line. As another alternative, sensor W2 could be sent in to a manufacturer or a vendor laboratory or even a national laboratory such as the National Institute of Standards and Technology for calibration. During calibration of sensor W2, web inspection system W3 may continue inspection of the web using its previously calibrated state. In some cases it may be desirable to configure web handling system W6 with a plurality (2, 3, or even more) of single output sensors, such that at any given time, at least one is on-line and receiving signals from web passing in lane W4, such that a calibrated signal is received from at least one single output sensor while any of the other single output sensor(s) is off-line being calibrated (and vice-versa).

Sensor W2, in one embodiment, is configured to measure the same property as web inspection system W3. For example, both sensor W2 and web inspection system W3 may in one embodiment be configured to respond to inspection signals (in this case light) in the range visible to humans. Alternatively, however, web inspection W3 may be configured to measure a property different than that measured by sensor W2, but strongly correlated to it. An example of a strongly correlated property is where sensor W2 measures thickness of the web via an ultrasonic transducer, and the web inspection system W3 is a line scan camera sensitive to light in the human-visible spectrum. Another example of a web property strongly correlated with light in the human-visible spectrum is, at least in some cases, thermal conductivity, discussed above.

Quantitative imaging system W5 may be an application-specific or general purpose computer with memory and a central processing unit that receives input from sensor W2 and web inspection system W3 and analyzes the input to apply, or in some embodiments determine, a calibration model for web inspection system W3. A calibration model is one or more numerical values or algorithms that define a mathematical relationship used to convert output signals from web inspection system W3 from raw data into calibrated units. There are two general calibration models that will be described herein. The first calibration model, which is the "sensor to inspection system calibration model" defines the mathematical relationship between sensor W3 and the portion of inspection system W3 associated with the same lane W4 as sensor W3. The second calibration model, which is the "cross-web calibration model" defines the mathematical relationship between lanes that comprise inspection system W3's cross-web field-of-view.

Quantitative imaging system 5 determines the cross-web calibration model by processing data sets associated with lane W4 (which would is calibrated to point sensor W2 via the sensor to inspection system calibration model) and data sets associated one or more lanes other than lane W4, as well as data describing the cross-web signal profile of the inspection system.

Quantitative imaging system W5 is shown in FIG. 1 as a single system, but in alternative embodiments it may be comprised of a plurality of computers, networked together or standing alone, that execute various software algorithms in support of the calibration techniques described herein.

Figure 2:
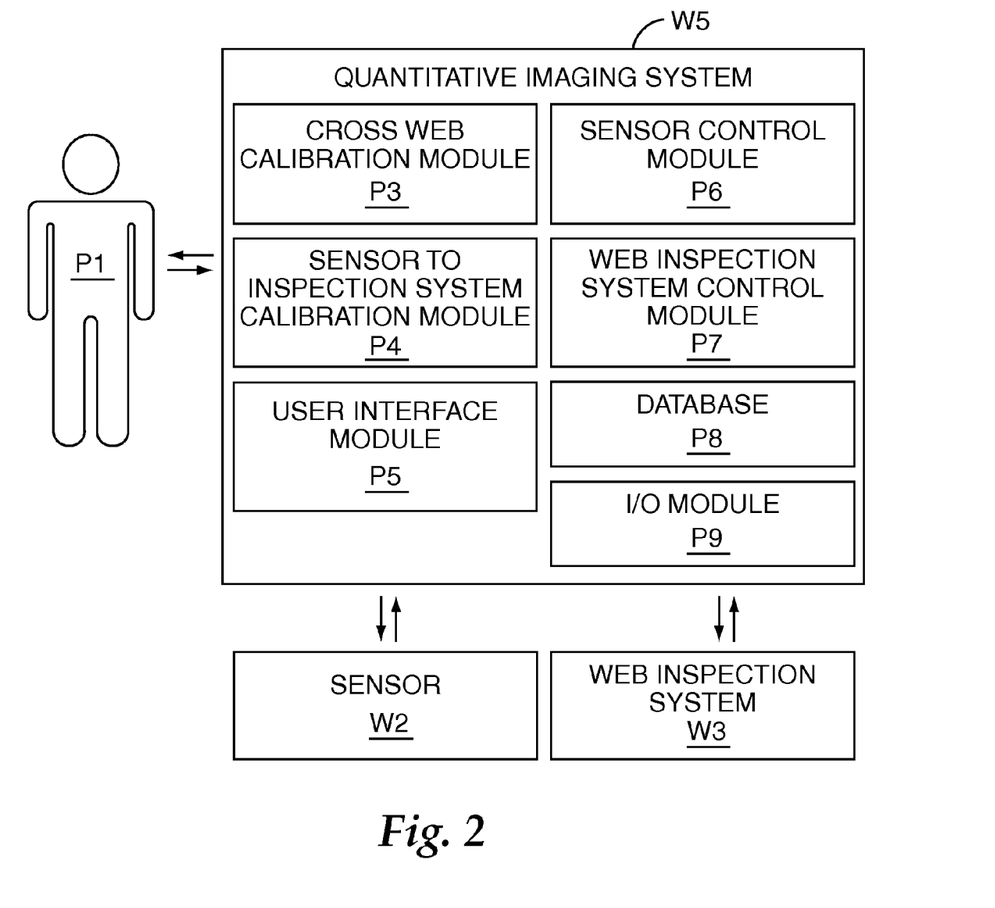
FIG. 2 is a diagram of functional modules that comprise a quantitative imaging system.

FIG. 2 is a diagram showing, in one example embodiment, the functional modules that comprise quantitative imaging system W5. FIG. 2 is described with respect to a discreet set of functional modules, but a skilled artisan will understand that this description is for illustrative purposes only, and that a system having the same or similar functionality may be architected in myriad ways. Each of the functional modules illustrated in FIG. 2 may communicate with any of the other modules; any of the modules may be implemented in hardware or software or some combination thereof. User P1 is any user of web inspection system W5. User P1 may be a human operator responsible for quality control on web W1. User P1 interacts with quantitative imaging system W5 primarily through a keyboard, a mouse, and a display of some sort (none of which are shown in FIG. 2). User interface module P5 may generate a graphical user interface or a command-line type interface on a display such that user P1 may both provide information to quantitative imaging system W5, and receive information from quantitative imaging system W5. In one embodiment, user interface module P5 generates windows on a display by calling on functionality provided by an operating system such as one marketed under the trade name "Windows" by Microsoft Corporation, Redmond, Wash. Other operating systems may be similarly used. User interface module P5 in turn provides and receives data and commands from other functional modules. There may be additional interfaces (not shown in FIG. 2) to automated web process control or web monitoring systems.

I/O module P9 interfaces with sensor W2 and web inspection system W3. I/O module P9 receives data streams from sensor W2 and web inspection system W3. In one example embodiment, depending on the particular implementation of quantitative imaging system W5, I/O module P9 also provides command and control information to sensor W2 and/or web inspection system W3. For example, elsewhere in this disclosure is described an embodiment of a cross-web transport device upon which sensor W2 is affixed, such that sensor W2 may move cross-web. I/O module P9, in such an embodiment, could provide control signals that dictate such cross-web movement. Also, I/O module P9 may provide other information to generally control either sensor W2 or web inspection system w3. Input received by I/O module P9 may be provided to other modules directly or stored in database P8 for subsequent analysis.

Database P8 is a data store implemented in a computer memory such as random access memory or a hard disk drive, or some combination thereof. It may be simply computer memory, a flat file, or a database such as that marketed by Microsoft Corporation of Redmond, Wash. under the trade name "SQL Server." Database P8 handles data storage needs of any of the functional modules that comprise quantitative imaging system W5. Data streams emanating from sensor W2 and web inspection system W3 may be stored in database P8, as well as data that comprise calibration models.

Web inspection system control module P7 provided command and control signals via I/O module P9 to web inspection system W3. The particular functionality supported by web inspection system control module P7 is dependant largely on the command and control interface provided by the particular web inspection system W3 chosen for implementation. For example, some line scan cameras that could comprise web inspection system W3 have application programming interfaces such to support a particular set of functionality; such functionality would exist in FIG. 2 within web inspection system control module P7. If web inspection system W3 has output that needs to be converted (for example, a raw voltage which needs to be converted into units), the means for conversion is implemented within web inspection system control module P7.

Sensor control module P6 is to the sensor control module P6 what web inspection system control module P7 is to the web inspection system W3, mutatis mutandis.

Sensor-to-inspection system calibration module P4 analyzes data from sensor W2 (provided via I/O module P9 and possibly stored in database P8) and web inspection system W3 and establishes the sensor to inspection system calibration model such that output from inspection system W3 associated with the same cross-web lane as sensor W2 is converted into the calibrated units of sensor W2's output. Examples of this conversion are provided below.

Cross web calibration module P3 determines, if necessary, and applies the calibration model provided by sensor-to-inspection system calibration module P4 to the other lanes of web W1 inspected by web inspection system W3, such that data from all lanes the comprise inspection system W3's field-of-view are calibrated to lane W3. Examples of such a calibration are provided below.

The functional modules described in association with FIG. 2 may have further functionality that is consistent with their general nature, but was not mentioned in this disclosure. Functionality described elsewhere that is not explicitly associated with a functional module listed in FIG. 2 exists within quantitative imaging system W5 generally. For example, the functionality that provides the alignment of signals emanating from sensor W2 and web inspection system W3 exists generally within quantitative imaging system W5.

Figure 3:
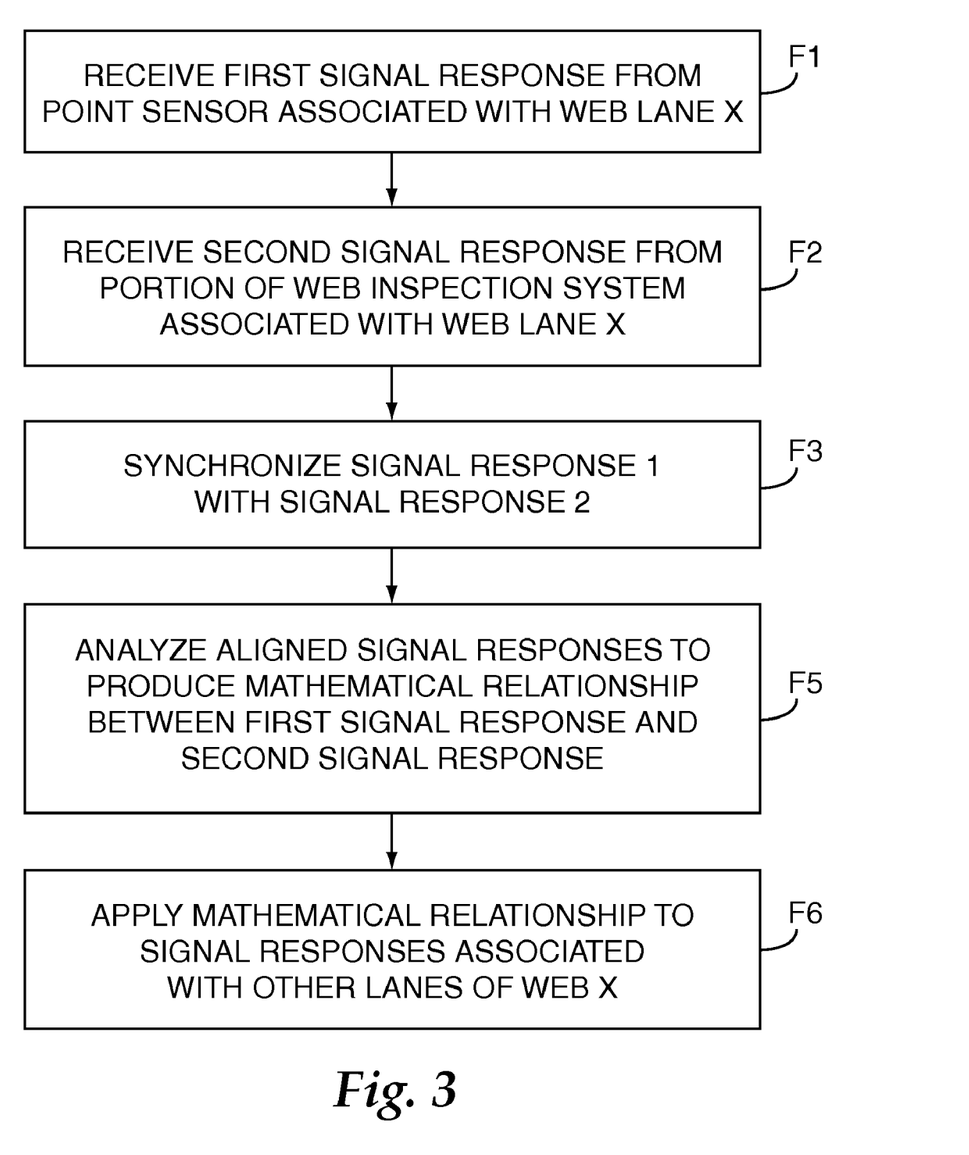
FIG. 3 is a flowchart illustrating a high-level process that may be used to calibrate a web inspection system.

FIG. 3 is a flowchart illustrating a high-level process that may be used to calibrate the web inspection system W3 that is shown in FIG. W. A first signal response is received from sensor W2, which, in this example, is located up-web from web inspection system W3 and associated with a particular "lane" of the web line (F1). In the context of FIG. F, this lane shall be referred to as lane X. Web inspection system W3 may inspect (i.e. receive signals from) the entire width of the web (or some portion thereof), but at least inspects lane X (F2). Signals from web inspection system W3 associated with lane X are for the purposes of FIG. 3 termed the second signal response. The first signal response is synchronized with the second signal response (F3) such that the signals from the single output sensor W2 and the lane-X portion of web inspection system W3 are representative of the same areas of web W1. If the distance between single output sensor W2 and web inspection system W3 is known, as well as the speed of the web, synchronization may be accomplished by determining the time it takes for a point along web W1 to go from single output sensor W2 to web inspection system W3. This time delay may be used to define a shift which may then be applied to the respective data stream emanating from either sensor W2 or web inspection system W3, thus time-synchronizing the data streams. Alternatively, encoders may be used to trigger sampling of points from sensor W2 and inspection array W3. The encoders trigger data acquisition at fixed space intervals of the web rather than fixed time intervals, such that the two data sets are spatially synchronizing.

When the shift value cannot be determined by measuring (or calculating) the time delay between sensor and web inspection system, data analysis techniques such as cross-correlation may be used to determine the shift value necessary to time synchronize data streams emanating from sensor W2 and web inspection system W3. These techniques are possible if data streams from sensor W2 and the lane-X portion of web inspection system W3 are similar such that linear cross-correlation methods are adequate to determine misalignments between the data sets. In some cases, data streams from sensing elements adjacent to lane-X of web inspection system W3 are compared with the data stream from sensor W2 in order to find the best cross-web alignment for lane-X. The cross-web spatial location on web inspection system W3 with the best correlation may vary slightly from the physical cross-web location of sensor W2 due to web steering or potentially even web stretching or shrinking. In other cases, where the cross-web spatial resolution of web inspection system W3 is of a finer scale than the lane-X sensed by sensor W2, the signal outputs from several adjacent elements of web inspection system W3 may be combined so as to better reflect the material in lane-X before the cross-correlation is carried out.

In certain embodiments, it may be advantageous to apply a variable transformation prior to cross-correlation in order to obtain a linear relationship between the data sets, especially in cases where a mathematical model exists for the response functions of the sensors. In other embodiments in which an unknown, possibly nonlinear relationship exists between the data sets, one may employ more general similarity metrics that are known in the art, such as mutual information. The procedure is analogous to that described below, in that the similarity metric is computed for several time shift values, and the data sets are aligned by choosing the time shift that maximizes the similarity metric.

The equations below show one approach to determining the shift value mathematically, in order to synchronize the data streams. The following equations are for non-normalized cross correlation followed by linear regression.

$$r(x_i, n) \equiv \sum_m f(x_i, y_m) g(x_i, y_{m+n})$$

f is the vector of calibrated single output sensor data in engineering units at a particular cross-web location, $x_i$, and g is the corresponding vector computed from appropriately weighted array sensor data at that location. Data sets from the sensor W2 and the web inspection system W3 associated with lane W4 may be sampled discretely in time or in space using an encoder trigger acquisition at fixed sampling distances. The results of the sampling are stored in computer memory, such as that of quantitative imaging system W5, for a finite down-web section of web in order to compute the summation. It is possible to mean-center the data before performing cross-correlation, and any of a number of well-known normalization methods may also be employed. The two data sets in this technique have the same number of samples (which may mean the sensor and the web inspection system sampled at the same rate, or it could mean that the one of the sets was reduced or expanded using statistical extrapolation techniques). In one embodiment, the sampling rates for sensor W2 and web inspection system W3 are identical, and the sensor and the web inspection system both resolve the same features in the property of interest. The peak of the cross-correlation output $$n^*(x_i) = \arg\max_n \{r(x_i, n)\}$$

identifies the shift between the two data sets owing to the transit time of the web between the locations of the single output sensor and the array sensor (or vice versa). This shift may then be applied to the data streams to achieve time-synchronization.

A combination of manual and statistical techniques may also be employed to determine the shift value to be applied to the data streams to achieve synchronization. For example, an estimate of the time it takes for a point on the web to move from sensor W2 to web inspection system W3 may be used to establish a window within which to use cross-correlation to get the more accurate data alignment from the peak of the cross-correlation result. The strength of the correlation coefficient can also be used as an indication of sensor errors, as the farther down web distance between the sensor and the web inspection system, the more web steering affects might reduce correlation.

Continuing with FIG. 3, with the data streams aligned, the first and second signal responses are next analyzed by quantitative imaging system W5 to produce a calibration model that define(s) the relationship between the respective signal response of sensor W2 (which will be called the first data stream for the purposes of this figure) and the area of web inspection system W3 associated with the same lane W4 as sensor W2 (which will be called the second data stream for the purposes of this figure).

The exemplary technique described herein uses linear regression to determine the relationship, and thus correlation factor, between the first and second data streams. Linear regression has been found to work sufficiently well for sensors with similar response functions over a finite range of the measured property. Other techniques may be better suited for other combinations of sensor and web inspection system responses. For example, when dealing with wider ranges of a measured property, local linear regressions could be done at fixed intervals between data sets (for example, after the passage of a certain amount of time or a certain distance of web) or automatically as determined by the magnitude of the measured property. If a nonlinear parametric model is known to relate the data sets, one may employ nonlinear least squares to fit the parameters of the model. In the case of an unknown model, more general nonparametric techniques are well-known in the art. For example, a kernel smoother may be applied to the observed curve relating aligned datasets in order to obtain a nonparametric estimate of the true relationship without recourse to any prior model.

A linear response model for the $i^{th}$ element of the array sensor with no cross talk between adjacent elements, may be written as $$\hat{f}(x_i,y_j) = \alpha_1(x_i)\tilde{g}(x_i,y_j) + \alpha_2(x_i)$$

where $\tilde{g}(x_i,y_j) = g(x_i, y_{j+n^*})$ is the aligned data vector, and $\hat{f}$ is the estimation vector for the calibrated output. The goal is to find the fitting coefficients, $\alpha$, that minimize the least squares error between the measured values from the calibrated sensor, f, and the values predicted by this model, $\hat{f}$, derived from the data from the $i^{th}$ element of the array sensor.

Thus, letting G be the matrix whose first column is the aligned and weighted array sensor data at position $x_i$ and f be the single column vector formed from the calibrated single output sensor data, also at position $x_i$, we then compute the scalar vector $\alpha$ to get the best fit linear scaling and offset values in the least-squares sense:

$$G_{j1}(x_i) = \tilde{g}(x_i, y_{j^*})$$

$$G_{j2} = 1 \quad\quad\quad (3a,b,c)$$

$$\alpha(x_i) = (G^T G)^{-1} G^T f$$

It is this scalar vector $\alpha$ that comprises the calibration factor (in this example).

The final step in calibrating the web inspection system is for calibration factors to be applied to remaining cross-web portions of web inspection system W3 (F6). This is termed cross-web calibration. Generally, the response of each of the sensor elements that comprise web inspection system W3 will vary such that each one may have a slightly different output signal for the same amount of optical energy (in this example) emanating from the sample being imaged. Hence, it is necessary to correct for variation in the responses of the individual elements in the web inspection system in order to obtain calibrated data from the entire web inspection system. In other words, for each sensor element that makes up the web inspection system, it is necessary to find the $\alpha$ vectors at each cross-web position, $x_i$. This problem is analogous to the "flat field" correction that is often applied to camera-based inspection systems. The key is how to do this efficiently in a case where there may be thousands of cross-web positions $x_i$ in the imaging inspection system.

The inspection system's non-uniform sensor element, or pixel, response, may arise from differences in both the "background level" from pixel to pixel, that is, the signal value (although low, it is not necessarily zero) recorded when the illumination source is turned off, and the "gain" level associated with the amount of increase in output signal associated with a given unit of increase in incident optical power falling on a pixel. If one were to turn off the illumination source, one could record a background signal, and if the camera response is linear, one could take another image of a uniformly bright "white" field and characterize the response of the changes in values associated with the pixels. If the camera response is nonlinear, more than just two points would be required to characterize the response.

Several difficulties arise when characterizing cross-web response variations, since background light levels, illumination source intensity profiles, and sensor response factors can all change with time. For example, assume inspection system W3 images the light transmitted by a reference sample along a line illuminated by light source (for example, a line light, laser scanner, or similar device) with a line scan camera. Define the intensity distribution along the imaged section created by the illumination source as I(x), the transmission of the sample as T(x), with the light collected by the inspection system from the web area A(x) and imaged onto the corresponding discrete sensor in the linear array whose response per unit of light is linear and given by R(x). Further assume that there can be a set of amplifiers, at least one for each pixel, that define gain along the array. Then if b(x) is the signal from the linear array when the illumination light source is off, the signal output along the linear array could be written as $$S(x) = g(x)*R(x)*T(x)*I(x)*A(x) + b(x), \text{ or combining terms, as}$$

$$S(x) = a(x)*T(x) + b(x)$$

The goal is to find a(x), and b(x), such that one can invert the measured signal S(x) and recover the property T(x) of the web material.

The transmission case above can be generalized to any web property Z(x) by defining $\zeta(x)$ as the fraction of light output to the inspection system per unit light input and per unit of property Z. Then the generalized form for the signal is $$S(x) = a(x)\zeta(x,Z)Z(x) + b(x,Z)$$

In many cases of interest, neither $\zeta(x)$ nor b(x) is a function of Z, so this can be written as $$S(x) = a(x)\zeta(x)Z(x) + b(x)$$

which we rewrite as $$S(x) = k\alpha(x)Z(x) + b(x)$$

where k is an constant scaling factor, such that $\alpha(x)$ is the relative signal response profile, consistent with our previous notation. Since the constant k will be found during the linear regression step described earlier, we only need find the relative profile $\alpha(x)$ to invert the signal and find Z(x). This important in practice because sometimes the cross-web profile calibration must be carried out using different overall gain or exposure levels than used during production so as neither to saturate nor underexpose the inspection system response. However, since $\alpha(x)$ now contains an additional function other than just the light source and pixel response variations, we can't in general simply image the light source intensity distribution to arrive at the desired profile, although this can be adequate when the property of interest is transmission. In many cases of interest, variations in b(x) with respect to x will be small relative to the signal levels at all x locations, so its dependence on x can be neglected, and its constant value can therefore be found during the linear regression step. Otherwise, b(x) can be recorded by storing the signal with a reference sample in place under normal ambient production conditions except with the illumination source turned off such that $\alpha(x) = 0$ everywhere.

We now define a time-averaged signal as $$\langle \hat{S}(x) \rangle = \frac{1}{T} \int_{t0}^{t0+T} S(x) dt = \frac{1}{T} \int_{t0}^{t0+T} [k\alpha(x)Z(x) - b(x)] dt$$

where T is an arbitrary time duration chosen to average out random fluctuations in measurement system noise and spatially random fluctuations in the web profile Z(x). The length of T may need to be adjusted according to the property being measured and the particular process, but methods for choosing the appropriate length for T based on statistical process measurements are well known in the art. Provided that instantaneous deviations from the mean profiles of α(x) and Z(x) are uncorrelated variables during the time window from $t_0$ to $t_0$+T, this becomes $$\langle \hat{S}(x) \rangle = k \langle \alpha(x) \rangle \langle Z(x) \rangle - \langle b(x) \rangle$$

where the quantities in <brackets> represent time averages.

The profiles of <α(x)> and <b(x)> tend to be relatively stable with time (that is, downweb distance) during a given run. Since values for k and b at a particular x location on the web sensor can be found essentially as often as desired using the calibration transfer method described above, the cross-web calibration problem is reduced to that of recording a relative cross-web profile <α(x)> that is valid over some reasonable duration of time (>>T) to the accuracy levels required for the measurement. If the profile of <α(x)> is found to drift slightly during a run, then a profile correction can be accomplished using calibrated web sensor data at only a few cross web locations as described below. A new recording for <α(x)> may be required whenever there is a substantive change to the inspection system, or whenever, for example, a new product configuration changes the profile associated with ζ(x).

Recording the relative cross-web calibration profile, α(x), may be accomplished in several ways. As a first example method, before the web is in production, a single calibration sample could be scanned across the field of view of each sensor in the inspection array to map out the relative cross-web response profile. As long as the property value, call it $Z_1$, of this sample is in the range of interest for the web and ζ is only a function of x and not of Z, the exact value of $Z_1$ wouldn't even have to be known.

A second example method of cross-web calibration is as follows. Before a web is in production, web inspection system W3 could image a contiguous section of a strip of material whose profile of the desired property has been measured across an area that corresponds to the area viewed by sensor elements that comprise web inspection system W3, and the positions measured along the sample strip could be registered with the corresponding elements in the inspection array. In such a case, the range of the desired property along the calibration strip does not need to be completely uniform, as long as the profile of values along the strip is known, the values lie within the operating range for a subsequent web run, and ζ is only a function of x and not of Z. The points on the strip may be physically registered with elements of the array, or cross-correlation analyses may be used to match the known profile along the strip to the measured response from the array elements.

A third example method for cross-web calibration is to acquire an image as the web is being produced, collect the cross-web section of web corresponding to that image, and then use another calibrated sensor to measure properties across the web sample at positions corresponding to those sampled by the inspection system array elements. Several "rows" or strips across the sample could be used to reduce the impact of noise from the different sensors. Once again, this method is straightforward as long as ζ is only a function of x and not of Z.

A fourth mode for performing the cross-web calibration in cases where ζ is only a function of x and not of Z is an iterative method that updates the cross-web calibration profile during production of the web. For this fourth mode of performing the cross-web calibration, web inspection system W3 is comprised of either several stationary web sensors W2 of similar make fixed at different cross web locations or a movable sensor W2, which can be located at several different cross web locations, or a combination thereof, together with a time-average image from the inspection image. The number of cross web sensor locations, call it M, however, is far less than the number of sensing locations, P, in a web inspection system W3 that is comprised of an imaging system (such as a line scan camera). The web sensor locations yield only a coarse estimate of the true time-average cross-web material property profile, <Z(x)>; in general, this is adequate, because a stable <Z(x)>, often one that is relatively uniform, is the target for well-controlled manufacturing process. So, for example, time averaged data from, say, three web sensors could be used to fit up to a second order profile for $<Z_{est}(x)>$. The fine spatial details in <α(x)> and <b(x)>, related to variations in the illumination intensity profile and the sensor response and gain factors, are contained within a time-average cross-web signal profile, <S(x)>. We therefore record <S(x)>, compute <α(x)> using the recorded <b(x)> profile and $<Z_{est}(x)>$ as an estimate of the true profile <Z(x)>. This process can be repeated, often with the inclusion of moving one of the point sensors to a new position cross-web position to update the accuracy of the $<Z_{est}(x)>$ profile and hence <α(x)>.

The primary issue that arises in this time-average method is that of distinguishing between cross web variations in the web property <Z(x)> that are constant with time, for example streaks, and variations in <α(x)> that are also constant with time, as might be caused by, for example, pieces of dirt fallen onto the illumination light source. Incorporating a repositionable sensor which can be driven to the location of the streak or to several positions along the profile to calibrate the actual web property values at those points solves this issue, again without calibrating each sensor in the array that comprises the inspection system in this example. Alternatively, one could purposely impart a relative change in the cross-web alignment between the inspection system and the web, for example by steering the web or translating the entire inspection system an amount Δx relative to the web. New profiles akin to <Z(x)> and <α(x−Δx)> could then be found as above, and spatial variations in the profiles could then be properly attributed to either <Z(x)> or <α(x)> by comparison to the profile data prior to the displacement. The amount of movement required would depend upon the levels of variation in <Z(x)> and <α(x)> and the signal-to-noise ratio of the time-average measurements. Other methods might also be readily apparent to one skilled in the art, for example employing dual inspection systems, such that the likelihood that both <$α_1$(x)> and <$α_2$(x)> corresponding to the response both inspection systems have cross-web profile disturbances at exactly the same cross-web locations at the same instant is negligibly small.

In some embodiments, the use of a time-average signal profile obtained during normal web production is used to correct for pixel-to-pixel response variations, and the small number of cross-web calibration points used to correct for slowly varying changes in the cross-web calibration model. The α($x_i$) vectors form a cross-web response profile, and could be used to transform the inspection system data into a calibrated, quantitative image of the cross- and down-web variations in the web properties. This mode has the advantage that it can be done while film is being produced on the line and updated periodically during a run.

So far we've dealt with the case where the signal dependence on Z is linear and separable. Cases of interest where $\zeta=\zeta(x,Z)$ also may arise, as, for example, with properties like porosity and surface roughness, when optical scattering is likely to be important. But this is still the situation that we desire as long as the light signal is monotonically correlated with the property Z, albeit in a nonlinear fashion. The simplest case occurs when the x and Z dependencies in $\zeta$ are separable, as in $$\zeta(x,Z)=\xi(x)\psi(Z)$$

then we simply define a new property $$Z'=\psi(Z)Z$$

and proceed as before, substituting $\xi(x)$ as necessary for $\zeta(x)$ in the above. In order to recover the property Z, we would need to know or separately calibrate the function $\psi(Z)$, and this function would have to remain stable during the run. In the case of example method 1, we would need a set of calibrated samples spanning the appropriate range of property values of interest, each scanned across the field of view of the web inspection system at the plane that the web would occupy during production. In example method 2, a set of calibrated strips could be used to span the desired property range. In example method 3, several cross-web samples may have to be collected and measured to characterize the response range of the web inspection system. In these instances, if the functional form of $\xi(x)$ is known a priori, a smaller number of calibrated samples could be used. In a mode employing the iterative method 4, the nonlinear methods described earlier would suffice.

A conceptually similar approach can also handle the most general case, with $\zeta=\zeta(x,Z)$. Assume we have a set of N calibration samples that span the desired calibration range with $\{Z_i\}_{i=1}^N$ known for each sample, and that the set of measured responses $\{S_i\}_{i=1}^N$ corresponding to these samples are recorded at multiple cross web positions, $x_j$. The number of cross-web positions, $j=1$ to M, that are required depends on the smoothness of the function $\zeta=\zeta(x, Z)$ and the accuracy to which one needs the final measurement. Our experience has shown that the number of cross-web calibration points, M, can be much less than the number of sensing elements in the inspection array, P, for the vast majority of cases of interest. Hence, the first estimate of $\zeta=\zeta(x, Z)$ can be obtained by fitting profiles through the M measurements for each of the N realizations of Z, as described above in methods 1-3. The cross-web profiles can then be iteratively updated as described in method 4. Examples of the analytical methods used to do this would be nonlinear least squares in cases where a parametric model for $\zeta=\zeta(x, Z)$ was available, and non-parametric kernel smoothing techniques in cases where the model for $\zeta=\zeta(x, Z)$ was unknown.

Figure 4:
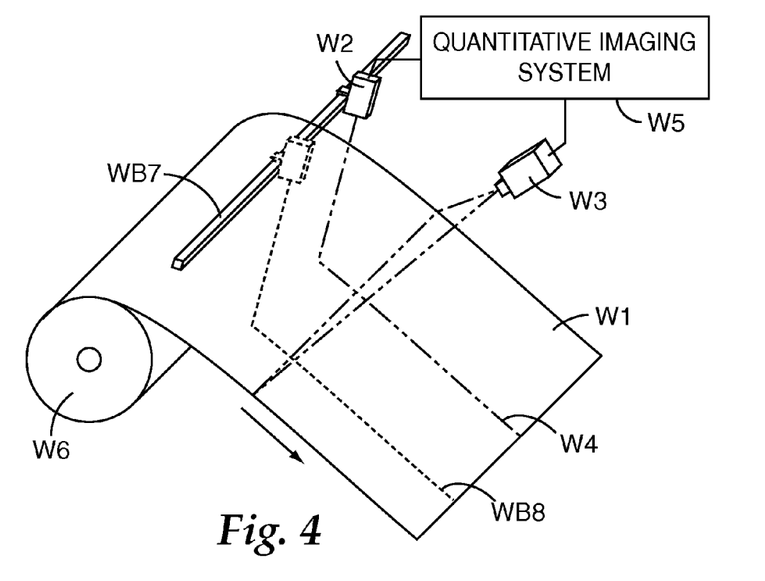
FIG. 4 is a schematic of a calibration system with a sensor mounted to a cross-web transfer device.

FIG. 4 shows a variation on the setup of the quantitative imaging system described above. FIG. 4 is the same as FIG. 1 except that sensor W2 is mounted on a cross-web transfer device WB7, which moves sensor W2 to several discreet cross-web locations, thereby exposing it to several web lanes, rather than only lane W4. For example, sensor W2 could be automatically moved (controlled by quantitative imaging system W5, for example) from a cross-web position associated with lane W4 to a second cross-web position associated with lane WB8. Enough samples along a down-web section of web are taken at each location so that the cross-correlation and regression method described earlier can be used at each point. And although the calibration at any given cross-web location is limited to the range of values spanned by the properties of the web over the sampled interval, the calibration can be easily re-done by returning the calibrated sensor to the same position relative to the array sensor. For example, after some amount of time has elapsed or some amount of web has gone by, or when the measured property has changed by a predetermined amount relative to the data range spanned by the previous calibration. In some cases, a perturbation or set of perturbations can be purposely added to the process to increase the range of the measured property sampled during the calibration.

With web inspection system W3's output thus calibrated, statistical processing methods, image processing algorithms and pattern recognition can be used to separate, classify, and track the severity of defects against benchmarks established in standardized metrics, such as in engineering units. Information about defects, now quantified in standardized metrics, can be used for on-line feedback on product quality, or combined with other process parameters to identify cause and effect relationships. Further, information on defects may be tracked over multiple runs to assess the impacts and tradeoffs associated with various process changes. The information about the defects may also be provided in conjunction with roll-maps to ensure a standardized, confirmable product quality level.

Figure 5:
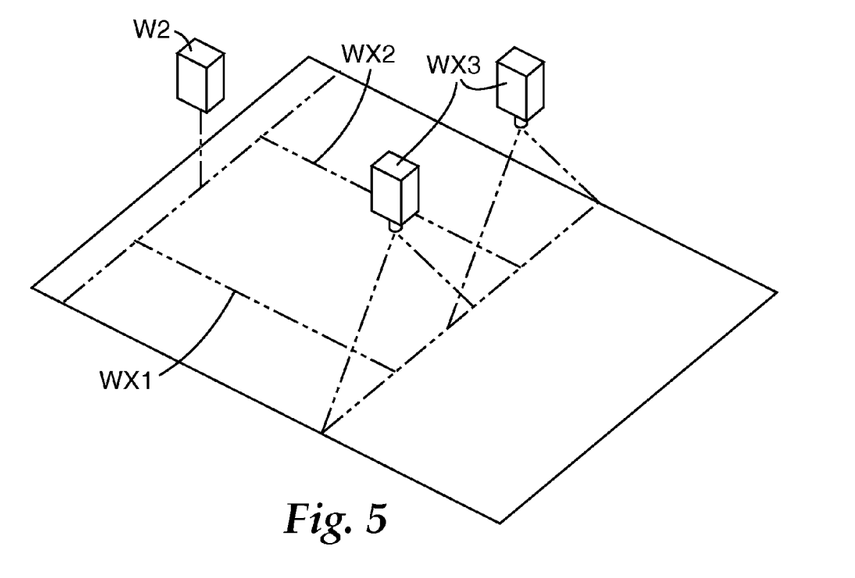
FIG. 5 is a schematic of a calibration system wherein the web inspection system includes two line-scan cameras.

A skilled artisan will recognize many variations on the system described thusly. For example, the system and methods thus described could be adapted for use with an web inspection system comprised of a plurality of line scan cameras. FIG. 5 shows one such system, where web inspection system W3 includes two line-scan cameras. Sensor W2 may be manually placed at lanes WX1 and WX2, which correspond to areas within the range of the first and second line scan cameras, respectively, that comprise web inspection system W3. Similarly, the sensor W2 could be mounted to a cross-web transfer device, as discussed earlier, which moves among a plurality of lanes, possibly corresponding cross-web range of web inspection system W3.

Example

Optical Density

We demonstrated the ability to measure the optical density of a carbon black coating on a web. The property of interest was the optical density of the carbon black coating at a wavelength of $\lambda=10604$ nanometers. Optical density, "OD," is a logarithmic measure of transmission, T, of the coated film, as $$OD(\lambda)=-\log_{10}[T(\lambda)] \quad (1)$$

where $$T = \frac{I - I_{bkg}}{I_0 - I_{bkg}} \quad (2)$$

and

I=light intensity transmitted through film
$I_0$=light intensity incident on film
$I_{bkg}$=background ambient light leakage with light source off and film present The carbon black coating obeys Beer's Law of absorption, so light transmitted through the film follows $$I(\lambda) = I_0(\lambda)(1 - r_{substrate}^2)\exp(-\alpha_{coating}(\lambda)l_{coating}) \quad (3)$$
$$\exp(-\alpha_{substrate}(\lambda)l_{substrate})$$
$$= I_0 T_{substrate}\exp(-\alpha_{coating}(\lambda)l_{coating})$$

where
- $\alpha_{coating}$ and $\alpha_{substrate}$ are the absorption coefficients of the coating and substrate, respectively, at the given wavelength
- $l_{coating}$ and $l_{substrate}$ are the physical thickness of the coating and substrate, respectively
- $r_{substrate}$ and $T_{substrate}$ are the amplitude reflection coefficient and the transmissivity of the substrate, respectively Hence, optical density is a nonlinear function of coating thickness, and it varies with wavelength. We installed and calibrated a custom near infrared (NIR) sensor to monitor the OD at 1060 nm (this sensor corresponding to sensor W2 in FIG. W). The target NIR OD for the coating layer was 0.8, and the substrate had $T_{substrate}=0.92$. The measured coated substrate OD=0.84, and an independent measure of coating thickness gave l=1.18 μm, which implied $\alpha(\lambda=1060 \text{ nm})=1.56 \text{ μm}^{-1}$. Thus, a variation of ±0.02 μm (±20 nm) in coating thickness corresponded to a ±3% change in transmission at $\lambda=1060$ nm.

A line scan camera and incandescent line light were used as the web inspection system (corresponding to web inspection system W3 in FIG. 1). This web inspection system was used to monitor the uniformity of coating transmission over about a 6" cross web field of view. The images were normalized using a time-averaged image taken through an uncoated substrate (using a shortened exposure time to bring the signal into range) to account for variations in light source intensity profile and camera response with cross-web position. The NIR sensor was located a distance of about d=12 inches up-web of the line imaged by the camera near the center of the camera field of view, and the data was sampled at the same frequency as the line rate of the camera, f. Since the web speed, v, was known, the time delay between the sensor and camera data streams was approximately d/v, and the NIR data could be shifted forward in time by fd/v points to approximately align the data sets. In many cases, such "manual" alignment is adequate, but the accuracy depends on the accuracy to which the separation distance, d, web speed, v, and sampling rate, f, are known. More exact alignment can be found by selecting the shift associated with the peak in the cross-correlation spectrum near this approximate value. Combining the cross-correlation method with the approximate values we knew from the experimental conditions allowed us to select the proper shift even in the presence of a somewhat periodic disturbance in the OD of the web.

There were no filters in front of the line scan camera, so the spectral response was that of a typical silicon charge-coupled device with a peak response wavelength at about 650 nm and minimal response below about 400 nm and above 1000 nm. In other words, there was no attempt to make the camera view the same spectral window as the NIR sensor. The details of spectral absorption profile over the camera response range were unknown, though we knew the transmission was lower when viewed over this range than out the outset. Neglecting background light leakage in both sensors, one can show that in this case, the effect of the substrate transmission is negligible, and the following approximation holds $$OD_{coating}(1060) = \frac{\alpha_{coating}(1060)}{\alpha_{coating}(vis)} OD_{coating}(vis) \quad (4)$$

such that for any given pixel on the camera, the OD at 1060 nm could be calculated from the visible transmission data as $$OD_{coating}(1060, \text{pixel}) = [-\log_{10}\{T(vis, \text{pixel})\} - 0.036]\left[\frac{\alpha_{coating}(vis)}{\alpha_{coating}(1060)}\right] \quad (5)$$

The 0.036 offset arises from the substrate transmission, and the last term in brackets is the calibration factor for converting the visible transmission data recorded by the camera into infrared OD units. Using our a priori knowledge of web speed and distance between sensor and camera allowed us to manually shift the data sets into alignment with the aid of side-by-side plots of the two data series. We then adjusted the scaling factor of $\alpha_{coating}$ (vis) in eqn (5) until we minimized the least squares difference between the aligned data sets, analogous to the regression method described earlier.

Example

Retardance and Orientation of Fast Axis for Birefringent Films

Point sensors and line scan cameras were configured to monitor optical properties of birefringent polypropylene film. In this case, the film stretching process orients polymer molecules and creates a "fast" optical axis nominally in the downweb direction, meaning that the refractive index in this direction is slightly lower than the refractive index measured 90° from this axis, that is, the "slow" axis. However, the fast axis is not constrained to align exactly in the downweb direction—downweb alignment is the target, but variations in the process cause the orientation to vary in the range of ±3° or so. Since the refractive indices along the fast and slow axes are unequal, light waves polarized along these axes become out of phase after propagating through the film. This is called retardation, where the in-plane retardance, $R_0$, of a birefringent film is defined as $$R_0 = (n_{FA} - n_{SA})d \quad (6)$$

where
- $n_{FA}$ is the refractive index along the fast axis (principle axis of film, close to but not necessarily exactly aligned with machine direction)
- $n_{SA}$ is the refractive index along the slow axis
- d is the film thickness The point sensors (corresponding to sensor W2 in FIG. 1) were setup such that the incident light passed in series through a polarizer, the film, an analyzer (a 2nd polarizer crossed with the $1^{st}$), and onto a detector. Both the fast axis orientation and retardance sensors had similar signal response equations:

$$V_i = A_i \sin^2(2(\beta_{FA} - \beta_{o,i}))\sin^2\left(\frac{\pi}{\lambda_i}R_0\right) + C_i \quad (7)$$

where
- i stands either for fast axis (FA) or retardance sensor
- V is the signal voltage
- A is a gain coefficient accounting for light source intensity, reflection losses, detector response, and amplifier gain $\beta_{FA}$ is the angle of the fast axis of the film, measured positive CW from the downweb machine direction $\beta_o$ is the angle of the 1st polarizer pass axis, measured positive CW from the downweb machine direction $\lambda$ is the wavelength of light used (determined by the wavelength of the source and any spectral filters in front of the detector), [nm]

$R_0$ is film retardance [nm]

C is an offset coefficient (generally near zero) accounting for background light that leaks through polarizers when no film is present, average depolarization of film, and non-zero amplifier offset.

The FA and retardance sensor responses differed only by the coefficients, A and C, and the angles of the polarizers, that is, nominal angles for $\beta_{o,FA}=-10°$ and $\beta_{o,ret}=-45°$. Values for A, C, and $\beta_o$ for each sensor were determined from a calibration procedure, and the source wavelength was known, so the two sensors together measured the unknowns $\beta_{FA}$ and $R_0$. Sensitivity analysis showed that when the gain coefficients were adjusted to map the signals into the range [0, 10 V] for films with $\beta_{FA}$ in the range [−5, 5°] and $R_0$ in the range [45, 85 nm], the film retardance values had to be taken into account when analyzing the FA response, whereas including the true FA angle of the film (compared to assuming a FA angle of) 0° had only a minor effect on the retardance value computed from the $R_0$ sensor.

Line scan cameras (corresponding to web inspection system W3 in FIG. 1) were setup down-web from the sensors to view polarized line lights through the film, and analyzers were mounted on the camera lenses and crossed with the respective polarizers that served as the illumination source. Except for the units of the digitized response, the camera pixels near the center of the field-of-view received signals at near normal incidence (to the web's surface) obey similar response equations to the above. Therefore by aligning the cameras such that the point sensors were within the center of the field of view and synchronizing the camera line rate with the sampling rate of the point sensors, could use the cross correlation and regression operations described earlier to transfer the calibrated responses of the $R_0$ and FA point sensors to the central pixels in the respective $R_0$ and FA cameras. Note that this operation uses only on-line data from production film; no calibration samples were used to characterize the response of these pixels.

We neglected FA orientation variations completely for the $R_0$ image, since this had only a minor effect, as noted above. For the FA image, we assumed as a first approximation that the $R_0$ value measured by the point sensor was uniform along the entire line viewed by the camera. This worked fairly well in this application, since chatter and casting wheel speed variations tended to dominate variations in $R_0$, and such variations show up as time-varying web thickness extending more or less uniformly across the web. In this way, we didn't need to register the two line scan cameras to ensure that the line arrays were exactly parallel, although such an operation could have been done.

What is claimed is:

1. A system comprising:
   an I/O module configured to receive a data stream emanating from a web inspection system that is configured to monitor a cross-web width of a web of material, the cross-web width defined by at least a first and a second lane;
   a cross-web calibration module configured to:
   a) associate portions of the data stream with the first and the second lane such to provide a first and second data stream associated respectively with the first and second lane;
   b) apply a first calibration model to the first data stream to convert the first data stream into calibrated units of measurement of a web property; and
   c) apply a second calibration model to the second data stream to convert the second data stream into the same calibrated units as the first data stream.

2. The system of claim 1, wherein the web inspection system is a line scan camera.

3. The system of claim 2, wherein the first and second lanes are characterized by a plurality of pixels.

4. The system of claim 1, wherein the I/O module further provides the first and second data streams, both in calibrated units, to a process control module that controls properties of a web manufacturing process.

5. The system of claim 1, wherein, after the first and second calibration models have been applied to the first and second data streams respectively, the data streams are analyzed to identify non-uniform portions of data that correspond to non-uniform areas of the web.

6. The system of claim 1, further comprising:
   a database module operative to store at least a portion of the first and second data streams after those streams have been calibrated by the cross-web calibration module.

7. The system of claim 1, further comprising:
   a database module operative to store a summary of at least a portion of the first and second data streams after those streams have been calibrated by the cross-web calibration module.

8. The system of claim 7, wherein the summary is comprised of a summary statistic.

9. The system of claim 1, wherein, in addition to the cross-web width being defined by at least a first and a second lane, the cross web length is further defined by a plurality of additional lanes, and wherein the cross-web calibration module is further configured to apply further respective calibration models to the respective plurality of additional lanes, such that each of the data streams is associated with each of the lanes that comprise the cross-web width is provided in the same calibrated units as the first data stream.

10. The system of claim 1, wherein the cross-web calibration module is additionally configured to:
    receive information characterizing the web inspection system's cross-web response profile, and based on that information, modify the second data stream before applying the second calibration model.

* * * * *

UNITED STATES PATENT AND TRADEMARK OFFICE
CERTIFICATE OF CORRECTION

| | | |
|---|---|---|
| PATENT NO. | : 7,957,000 B2 | |
| APPLICATION NO. | : 12/786975 | |
| DATED | : June 7, 2011 | |
| INVENTOR(S) | : David L Hofeldt | |

It is certified that error appears in the above-identified patent and that said Letters Patent is hereby corrected as shown below:

Column 9

Line 17; delete " $\hat{f}(x_i, y_j) = \alpha_i(x_i)\tilde{g}(x_i, y_j) + \alpha_2(x_i)$ " and insert -- $\hat{f}(x_i, y_j) = \alpha_1(x_i)\tilde{g}(x_i, y_j) + \alpha_2(x_i)$ -- therefor.

Column 11

Line 19; delete " $\langle \hat{S}(x) \rangle = k'\langle \alpha(x) \rangle\langle Z(x) \rangle - \langle b(x) \rangle$ " and insert -- $\langle \hat{S}(x) \rangle = k'\langle \alpha(x) \rangle\langle Z(x) \rangle - \langle b(x) \rangle$ -- therefor.

Column 17

Line 25; delete "of)0°" and insert --of 0°)-- therefor.

Signed and Sealed this
Tenth Day of April, 2012

David J. Kappos
*Director of the United States Patent and Trademark Office*